United States Patent
Djeu et al.

(10) Patent No.: US 8,736,835 B2
(45) Date of Patent: May 27, 2014

(54) DUAL-GAS MICROCAVITY RAMAN SENSOR AND METHOD OF USE

(71) Applicants: Nicholas Djeu, Tampa, FL (US); Andreas Muller, Tampa, FL (US)

(72) Inventors: Nicholas Djeu, Tampa, FL (US); Andreas Muller, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/080,283

(22) Filed: Nov. 14, 2013

(65) Prior Publication Data

US 2014/0071446 A1    Mar. 13, 2014

Related U.S. Application Data

(63) Continuation-in-part of application No. 13/542,282, filed on Jul. 5, 2012, now Pat. No. 8,599,373.

(60) Provisional application No. 61/505,270, filed on Jul. 7, 2011.

(51) Int. Cl.
*G01J 3/44* (2006.01)

(52) U.S. Cl.
USPC .......................................... 356/301; 356/454

(58) Field of Classification Search
CPC .......... G01N 21/65; G01N 21/658; G01J 3/44
USPC ........... 356/36, 244, 300–303, 311, 317, 318, 356/417, 451, 452, 454
See application file for complete search history.

(56) References Cited

U.S. PATENT DOCUMENTS

| | | | |
|---|---|---|---|
| 4,057,349 A * | 11/1977 | Barrett | 356/45 |
| 4,648,714 A | 3/1987 | Benner et al. | |
| 4,784,486 A | 11/1988 | Van Wagenen et al. | |
| 5,255,067 A | 10/1993 | Carrabba et al. | |
| 2004/0075845 A1 * | 4/2004 | Chang | 356/519 |
| 2006/0183236 A1 * | 8/2006 | Berlin et al. | 436/94 |

OTHER PUBLICATIONS

Kippenberg et al., Theoretical and Experimental Study of Stimulated and Cascaded Raman Scattering in Ultrahigh-Q Optical Microcavities. IEEE Journal of Selected Topics in Quantum Electronics. 2004. vol. 10 (No. 5): 1219-1228.

Li et al., Near-confocal cavity-enhanced Raman spectroscopy for multitrace-gas detection. Optics Letters. 2008. vol. 33 (No. 18): 2143-2145.

Linder et al., 900 mW continuous wave operation of AlInGaP tapered lasers and superluminescent diodes at 640 nm. Lasers and Electro-Optics. 2004: 900-901.

* cited by examiner

*Primary Examiner* — Tarifur Chowdhury
*Assistant Examiner* — Michael P LaPage
(74) *Attorney, Agent, or Firm* — Molly Sauter; Smith & Hopen, P.A.

(57) ABSTRACT

In accordance with the present invention, a dual-gas Raman sensor is provided that is based on an enhanced spontaneous dual emission as a result of cavity quantum electrodynamic effects. The dual-gas sensor includes a first reflector that exhibits a high reflectivity near the Raman shifted emission for the first species of interest and a moderate reflectivity near the Raman shifted emission for the second species of interest and a second reflector that exhibits a high reflectivity near the Raman shifted emission for the first species of interest and a moderate reflectivity near the Raman shifted emission for the second species of interest, allowing for the simultaneous measurement of the density of both the first species of interest and the second species of interest.

20 Claims, 3 Drawing Sheets

DUAL-GAS MICROCAVITY RAMAN SENSOR AND METHOD OF USE

CROSS-REFERENCE TO RELATED APPLICATIONS

The present invention claims priority to co-pending U.S. Non-Provisional patent application Ser. No. 13/542,282, filed on Jul. 5, 2012 and entitled "Microcavity Raman Sensor and Method of Use", which claims priority to U.S. Provisional Patent Application No. 61/505,270, filed on Jul. 7, 2011 and entitled "Microcavity Raman Sensor and Method of Use".

BACKGROUND OF THE INVENTION

When a Raman active medium is placed in an optical cavity, a large enhancement in the scattering efficiency can be realized. The enhancement can be observed when the cavity is made resonant with either the wavelength of the excitation light or the wavelength of the Raman scattered light. The effect is maximized when the cavity is made simultaneously resonant with both, i.e., when a double resonance is obtained. The exact magnitude of the enhancement depends on, among other factors, the finesse of the cavity at the two wavelengths and the volume of the mode sustained by the microcavity.

In the prior art the double resonance condition could be achieved only for a very thin solid sample with a thickness of less than one wavelength. The sample was made to have plane parallel surfaces, effectively creating a planar resonator with two flat partial reflectors forming the cavity. Because of the fixed spacing of the cavity, resonance with the wavelength of the excitation light could be established only for an off-axis laser beam. As a result, the resonance was accompanied by a high walk-off loss. Furthermore, planar resonators are inherently only quasi-stable, and are therefore precluded from having a high finesse even for axial beams because of diffraction. In addition, the extension of this approach to fluid samples is not described in the prior art.

Accordingly, what is needed in the art is a microcavity arrangement capable of sustaining the double resonance condition with high finesse for Raman scattering in fluids, thereby providing for the measurement of the concentration of one or more species of interests in a fluid sample.

SUMMARY OF THE INVENTION

In accordance with the present invention is provided a novel Raman sensor based on quantum electrodynamic effects capable of detecting trace amounts of chemicals in gases and liquids with a high degree of accuracy.

In accordance with the present invention, an ultra-sensitive chemical sensor is provided that is based on an enhanced spontaneous Raman emission as a result of cavity quantum electrodynamic effects. More specifically, the sensor in accordance with the present invention makes use of a double resonance of a stable Fabry-Perot microcavity with both the excitation laser frequency and the Raman frequency. As such, the Raman shift corresponds to an integer times the free spectral range of the microcavity. Because the Raman frequency directly depends on the excitation laser's frequency, the fulfillment of the resonance condition for the excitation laser frequency guarantees that resonance with the Raman frequency is also satisfied.

In a particular embodiment, a Raman sensor for detecting the concentration of a single species of interest in a sample may include a first substantially flat reflector and an adjustable optical fiber, wherein the adjustable optical fiber is translatable in a direction parallel to the fiber optic axis of the optical fiber, and a second substantially concave reflector positioned at a proximate end of the optical fiber and aligned substantially parallel to the first reflector, the second reflector separated from the first reflector by a distance to form a microcavity having a microcavity length equal to the distance between the first reflector and the second reflector, wherein the microcavity length is dependent upon the Raman transition of a species of interest to be detected. The sensor may further include an excitation laser positioned to emit an excitation wavelength incident upon the first reflector and the second reflector, wherein the wavelength of the excitation laser is dependent upon the microcavity length between the first reflector and the second reflector and a Raman emission signal detector positioned to receive the Raman emission coupled out of the first reflector and to detect the concentration of the species of interest within a sample positioned between the first reflector and the second reflector.

In operation of the single-gas sensor, a sample containing a species of interest is introduced into a microcavity having a microcavity length dependent upon the Raman emission of the species of interest. An excitation laser signal having a wavelength determined by the microcavity length is then introduced into the microcavity. The Raman emission of the sample is then measured to determine the concentration of the species of interest within the sample.

In an additional embodiment, a dual-gas Raman sensor for detecting the concentration of a first species of interest and a second species of interest in a sample is provided. In this embodiment, the dual-gas sensor includes a first reflector that exhibits a high reflectivity near the Raman shifted emission for the first species of interest and a moderate reflectivity near the Raman shifted emission for the second species of interest and a second reflector that exhibits a high reflectivity near the Raman shifted emission for the first species of interest and a moderate reflectivity near the Raman shifted emission for the second species of interest. The second reflector is positioned at a proximate end of an optical fiber and aligned substantially parallel to the first reflector. The second reflector is separated from the first reflector by a distance to form a microcavity having a microcavity length equal to the distance between the first reflector and the second reflector, wherein the microcavity length is dependent upon the Raman transition of the first species of interest to be detected. An excitation laser positioned to emit at an excitation wavelength incident upon the first reflector and the second reflector is used to provide the excitation source for the microcavity. The wavelength of the excitation laser is dependent upon the microcavity length between the first reflector and the second reflector. To measure the relative density of the two species in the sample, a first Raman emission signal detector positioned to receive the Raman emission coupled out of the first reflector and to detect the concentration of the first species of interest within a sample positioned between the first reflector and the second reflector and a second Raman emission signal detector positioned to receive the Raman emission coupled out of the first reflector and to detect the concentration of the second species of interest within a sample positioned between the first reflector and the second reflector.

In operation of the dual-gas sensor, a sample containing a first species of interest and a second species of interest is introduced into a microcavity having a microcavity length dependent upon the Raman emission of the first species of interest. An excitation laser signal having a wavelength determined by the microcavity length is then introduced into the microcavity. A first Raman emission of the sample is measured to determine the concentration of the first species of interest in the sample and a second Raman emission of the sample is simultaneously measured to determine the concentration of the second species of interest in the sample.

To couple the laser beam into the microcavity, the present invention may include a dichroic filter positioned between the excitation laser and the first reflector, the dichroic filter having high reflectance at the wavelength of the excitation laser and high transmittance at the Raman emission wavelength.

To mode match the laser beam into the microcavity and to collimate the Raman emission coupled out of the first reflector onto the Raman emission signal detector, the present invention may include a lens positioned between the first reflector and the dichroic filter.

In a particular embodiment, the optical fiber may further be positioned within a close fitting ferrule to constrain the optical fiber and to allow translation of the optical fiber in the direction parallel to the fiber's optic axis.

The present invention may further include an excitation light detector positioned at a distance from the distal end of the optical fiber to detect the transmitted laser power and a piezoelectric transducer coupled to a distal end of the optical fiber to adjust the length of the microcavity by translating the optical fiber in the direction parallel to the fiber's optic axis dependent upon the detected excitation laser power.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE INVENTION

The ability of a cavity-resonant electric field to influence the spontaneous emission rate of an atomic transition is well known. In the case of Raman scattering, the rate of Raman photons spontaneously emitted into the cavity mode per molecule can be written as:

$$A_c = \frac{c^3 v_L \phi}{3 v_R^3 V (\Delta v_C + \Delta v_R)} \frac{d\sigma}{d\Omega} \quad (1)$$

where $v_L$ and $v_R$ are the frequencies of the laser and Raman photons, $\phi$ is the laser photon flux density, V the cavity mode volume at the Raman wavelength, $\Delta v_c$ the cavity linewidth at the Raman wavelength, $\Delta v_R$ the Raman transition linewidth, and $d\sigma/d\Omega$ the differential Raman scattering cross section. If there are $n_V$ molecules responsible for the Raman scattering in the mode volume, then the total rate of emission into the cavity mode can be found from:

$$n_V A_c = \frac{c^3 NLP}{3hV v_R^3 (\Delta v_C + \Delta v_R)} \frac{d\sigma}{d\Omega} \quad (2)$$

where N is the density of molecules of interest, L is the cavity length, P is the intracavity laser power, and h is Planck's constant. The differential scattering cross section itself varies as the fourth power of the Raman shifted frequency, making the net emission rate into the cavity mode vary approximately as the square of $v_R$ for a fixed pump photon flux density.

Thus, the result given in Eq. (2), along with the laws governing the scaling of Gaussian modes with changes in the resonator's dimensions, shows that for a given excitation laser power. Raman emission into the cavity mode is increased as the resonator mode volume is decreased.

For fundamental Gaussian modes, the double resonance condition requires that:

$$\frac{mc}{2nL} - \frac{m'c}{2nL} = \Delta v_V \quad (3)$$

where $\Delta v_V$ is the Raman frequency, m and m' are integers and n is the refractive index of the sample (the same refractive index is assumed for both the laser and Raman shifted wavelengths, because they are generally very close to each other).

When the frequencies are expressed in terms of wavenumbers, Equation (3) may be written as:

$$\frac{\Delta m}{2nL} = \Delta \bar{v}_V \quad (4)$$

Thus it is seen that only a discrete set of cavity lengths are permitted for any given Raman transition. These cavity lengths in turn dictate a discrete set of permissible excitation laser wavelengths.

Figure 1:
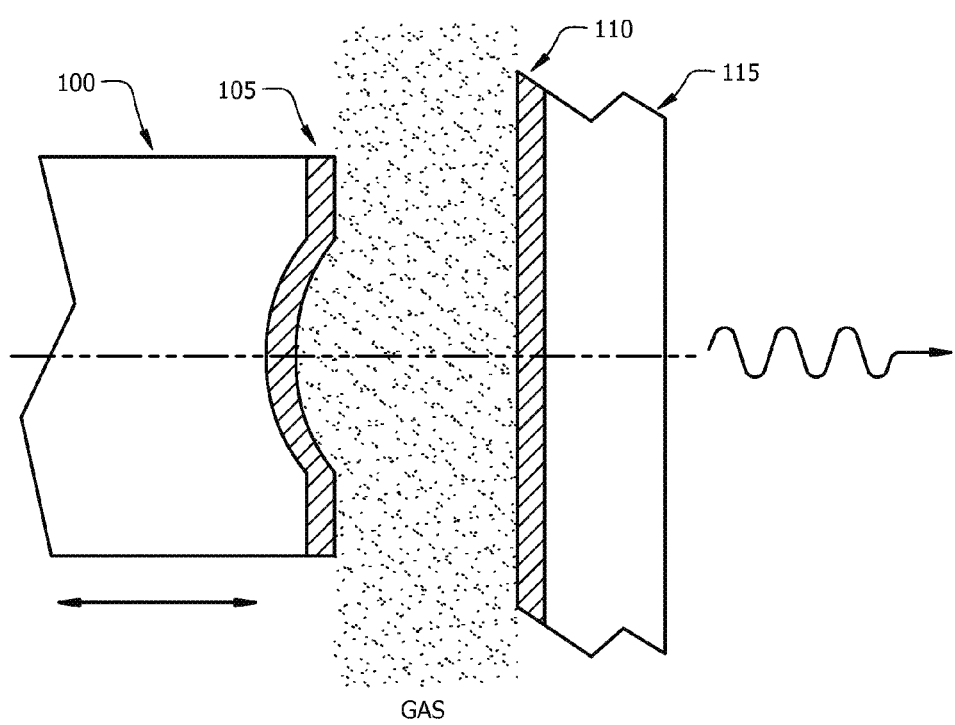
FIG. 1 illustrates the single-gas doubly resonant Fabry-Perot microcavity in accordance with an embodiment of the present invention.

With reference to FIG. 1, in one embodiment the microcavity is comprised of a concave reflector 105 fabricated at the end of an optical fiber 100 and a flat (or slightly concave) reflector 110 deposited on a thin substrate 115. The concave reflector 105 conforms to a spherically shaped crater formed in a polished end of the optical fiber 100. This micro-indentation feature can be created, for example, by the process of ablation with the use of one or more pulses of a focused beam from a $CO_2$ laser. The reflectors 105 and 110 can be produced, for example, by ion beam sputtering, which is known to be capable of yielding coatings with extremely high reflectivities. The sample from which Raman emission is sought is made to fill the space between mirrors 105 and 110. For maximum enhancement of the Raman emission from the sample, the reflectivities of the mirrors should be made as large as possible at both the wavelength of the excitation laser and the wavelength of the Raman emission.

In a preferred embodiment, the reflector 110 is kept in a fixed position while the reflector 105 is constrained to be translatable only in the direction parallel to the fiber 100 axis. The excitation laser beam is made incident into the microcavity from the right in FIG. 1. Raman emission from the sample is coupled out of the microcavity through the reflector 110.

Figure 2:
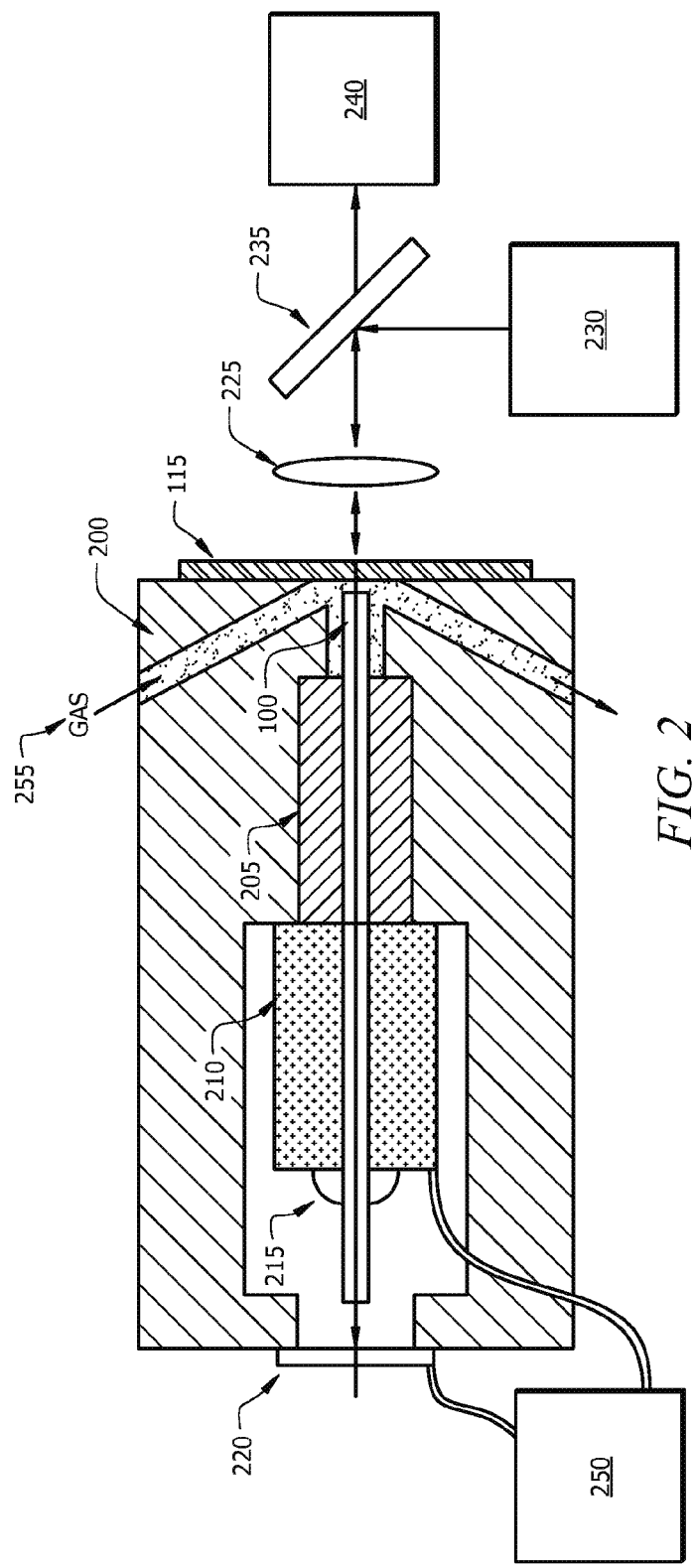
FIG. 2 is a schematic diagram illustrating the single-gas doubly resonant microcavity Raman sensor in accordance with an embodiment of the present invention.

A schematic illustrating the overall Raman sensor is shown with reference to FIG. 2. Output from a stabilized laser 230, tuned to the appropriate excitation wavelength, is made incident on a dichroic reflector 235, which is highly reflective at the excitation wavelength and highly transmitting at the Raman emission wavelength. The laser light from the stabilized laser 230 is then mode matched into the microcavity 200 with the use of lens 225. The optical fiber 100 is inserted into a close fitting ferrule 205 which permits free translation in the direction parallel to the fiber's optic axis. At the other end of the ferrule 205 the fiber 100 is attached to a piezoelectric transducer 210 with the use of adhesive 215. The laser light exiting the fiber is made incident on detector 220. The output from the detector 220 is used to keep the microcavity 200 always resonant with the excitation laser wavelength through the use of feedback electronics 250. The piezoelectric transducer 210 may adjust the cavity length (i.e. separation between the reflectors 105, 110 of FIG. 1) as necessary for initial set-up as well as during subsequent operation of the sensor to compensate for any dimensional changes due to temperature variations. The Raman emission coupled out of the flat reflector 110 positioned on the substrate 115 of the microcavity is collimated by lens 225, passed through the dichroic filter 235, and made incident on detector 240. Once the system has been calibrated, the Raman signal measured by detector 240 will directly provide the concentration of the species of interest from the sample 255 introduced into the microcavity 200, which produces the Raman emission.

In an exemplary embodiment, the capability of the doubly resonant microcavity Raman sensor will now be illustrated in the context of its application to the measurement of atmospheric $CO_2$ concentration. Suppose the 1,388 $cm^{-1}$ Raman transition in $CO_2$ is to be employed and the microcavity is semi-confocal. Then one possible cavity length is 25 µm (for $\Delta m=7$), and one possible excitation laser wavelength is 640 nm (for m=78), with a corresponding Raman emission wavelength of 702 nm. The differential Raman cross section for the 1,388 $cm^{-1}$ transition for 640 nm excitation is approximately $2(10)^{-31}$ $cm^2/sr$.

Suppose further that a laser power of 100 mW is available and that the microcavity mirrors (105, 110) have a reflectivity of 99.99% at both 640 nm and 702 nm. At a typical atmospheric $CO_2$ concentration of 400 ppm and for an expected Raman linewidth of around 0.2 GHz, one calculates a Raman emission rate through mirror 110 of $5(10)^6$ photons/s with the use of Eq. (2). If the detector 240 is a single photon counter and a measurement time of 1 second is employed, then a shot noise of approximately $2(10)^3$ counts can be expected. This implies that changes in the $CO_2$ concentration of about 0.2 ppm (i.e. 0.05% relative change) should be detectable with a response time of 1 second.

In an additional embodiment, the microcavity sensor may be modified to simultaneously measure emission from two Raman transitions, thereby providing a dual-gas microcavity sensor that is capable of simultaneously measuring the concentration of two different gases or liquids in a given sample.

In the dual-gas microcavity sensor, when measuring the concentration of a first species and a second species within a given sample, if the reflectivity of the micromirrors of the microcavity at the Raman shifted wavelength of the second species is relatively low, significant enhancement is still possible even when the microcavity is not exactly resonant with the wavelength of the second species. This realization makes possible the simultaneous measurement of the density of a first (trace) species relative to that of a second (majority) atmospheric gas, such as $N_2$ or $O_2$.

Neglecting phase changes at the mirrors of the microcavity and assuming unit refractive index for air, the double resonance condition is given by:

$$\frac{\Delta m}{2L} = \Delta \bar{v}_V \quad (5)$$

where $\Delta m$ is an integer, L is the microcavity length, and $\Delta \bar{v}_V$ represents the Raman shift. The sharpness of the double resonance is given by the width of the tuning curve:

$$\delta \bar{v} = (\bar{v}/\Delta \bar{v}_V)(\Delta \bar{v}_R + \Delta \bar{v}_C) \quad (6)$$

where $\bar{v}$ is the laser frequency at the peak of the double resonance, $\Delta \bar{v}_R$ is the Raman linewidth (typically 0.1 $cm^{-1}$ at 1 atm.), and $\Delta \bar{v}_C$ is the cavity linewidth ($<<\Delta \bar{v}_R$ for mirror reflectivities higher than 99.9%). Therefore, for a typical laser frequency of 10,000 $cm^{-1}$, the width of the tuning curve is $\delta \bar{v} \sim 1$ $cm^{-1}$. Thus, the chances of satisfying the double resonance condition for two arbitrary Raman transitions (i.e. a first species and a second species) is on the order of 1 in 1,000. Adjusting to account for the non-unity values of the refractive index of air and the phase shifts at the mirrors does not materially alter this estimate.

In the present invention, instead of attempting to realize two strong double resonances with high micromirror reflectivity at both Raman shifted wavelengths, a microcavity sensor is implemented in which the reflectivity at the second Raman shifted wavelength is low. For example, assume that the reflectivity at the second Raman shifted wavelength is only 30%. Then, for a typical microcavity length of L=30 µm. $\Delta \bar{v}_C \sim 20$ $cm^{-1}$ and $\delta \bar{v} \sim 200$ $cm^{-1}$. The calculated value is larger than the free spectral range of the microcavity. Hence, the Raman shifted wavelength for the second species is always going to be near the peak of a microcavity mode in the case of a weak double resonance. Nevertheless, significant enhancement for the Raman emission from the second species can still be realized.

In an exemplary embodiment, the first species of interest to be detected is $CO_2$ with a Raman shift of 1,388 $cm^{-1}$ and the second species of interest to be detected is $N_2$ with a Raman shift of 2,329 $cm^{-1}$. The Raman photon emission rate into the microcavity mode for a confocal resonator relative to that in free space into the same solid angle at the peak of the double resonance can be written as:

$$\rho = (12\lambda_R)/[\pi^2 L(\lambda_L + \lambda_R)(\Delta \bar{v}_R + \Delta \bar{v}_C)] \quad (7)$$

where $\lambda_L$ and $\lambda_R$ are the laser and Raman shifted wavelengths, respectively. For $\lambda_L=515$ nm and $\lambda_R=585$ nm (as appropriate for $N_2$), L=30 µm, $\Delta \bar{v}_R=0.1$ $cm^{-1}$ and $\Delta \bar{v}_C=20$ $cm^{-1}$, the enhancement in the Raman photon emission rate is $\rho=11$.

In order to satisfy the strong double resonance for $CO_2$ with $\lambda_L=515$ nm, it can be seen from Equation 5 that the cavity length needs to be 28.8 µm for $\Delta m=8$. For the same cavity length, the weak double resonance for $N_2$ would be detuned by 72 $cm^{-1}$ with $\Delta m=13$. But, since the width of the tuning curve is ~200 $cm^{-1}$, an approximately ten-fold enhancement can still be expected over the case where the microcavity is only slightly resonant with the excitation laser wavelength. Since $N_2$ is more than $10^3$ times more abundant than $CO_2$ in air, the two Raman emission signals are of comparable magnitude.

Figures 3A, 3B:
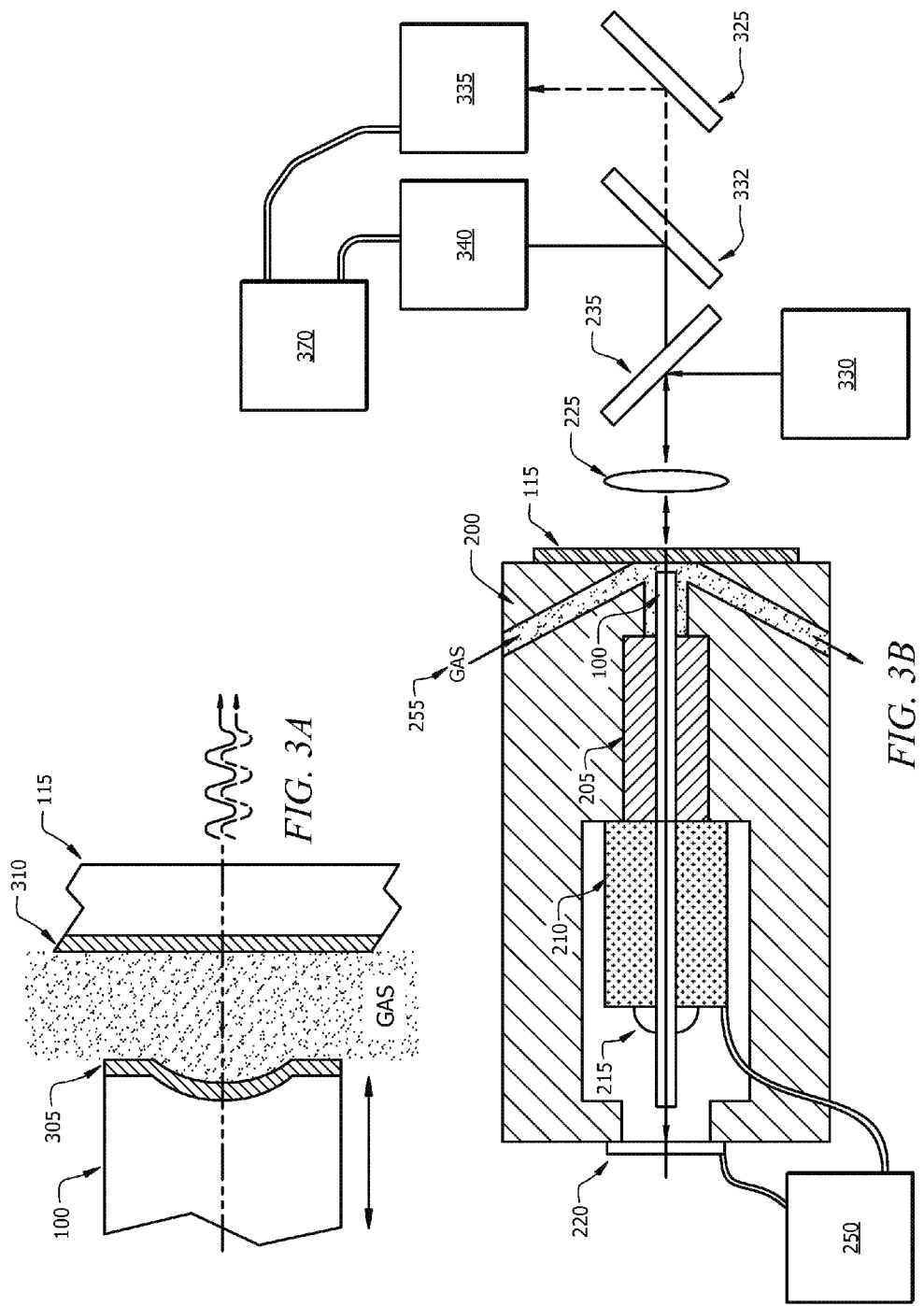
FIG. 3A illustrates the dual-gas doubly resonant microcavity Fabry-Perot microcavity in accordance with an embodiment of the present invention
FIG. 3B is a schematic diagram illustrating the dual-gas doubly resonant microcavity Raman sensor in accordance with an embodiment of the present invention.

With reference to FIGS. 3A and 3B, a dual-gas Raman sensor in accordance with the present invention for detecting the concentration of a first species of interest in a sample and a second species of interest in a sample is illustrated. The dual-gas sensor includes a first reflector 310 that exhibits a high reflectivity near the Raman shifted emission for the first species of interest and a moderate reflectivity near the Raman shifted emission for the second species of interest and a second reflector 305 that exhibits a high reflectivity near the Raman shifted emission for the first species of interest and a moderate reflectivity near the Raman shifted emission for the second species of interest. The second reflector 305 is fabricated at the tip on an optical fiber (100 of FIG. 1) and aligned substantially parallel to the first reflector 310. The second reflector 305 is separated from the first reflector 310 by a distance to form a microcavity having a microcavity length equal to the distance between the first reflector 310 and the second reflector 305, wherein the microcavity length is dependent upon the Raman transition frequency of the first species of interest to be detected. An excitation laser 330 is positioned to emit at an excitation wavelength incident upon the first reflector 310 and the second reflector 305, wherein the wavelength of the excitation laser 330 is dependent upon the microcavity length between the first reflector 310 and the second reflector 305. A first Raman emission signal detector 340 is positioned to receive the Raman emission coupled out of the first reflector 310 and to detect the concentration of the first species of interest within a sample positioned between the first reflector 310 and the second reflector 305. A second Raman emission signal detector 335 is positioned to receive the Raman emission coupled out of the first reflector 310 and to detect the concentration of the second species of interest within a sample positioned between the first reflector 310 and the second reflector 305.

In a particular embodiment, the first reflector 310 may be fabricated on a substantially planar substrate and the second reflector 305 may conform to a spherically shaped depression formed within a polished end of the optical fiber. In an exemplary embodiment, the radius of curvature of the first reflector 310 may be approximately planar and the radius of curvature of the second mirror 305 may be approximately 50 µm.

After the initial alignment has been performed, the distance (L) between the first reflector 310 and the second reflector 305, and as such the length of the microcavity, is controlled by a piezoelectric transducer 210 coupled to the second reflector 305. The length of the microcavity is controlled by feedback electronics 250 to guarantee that the tunable laser 330 is always on resonance. In a particular embodiment, the laser 330 is mode-matched to the microcavity 200 using a single aspheric lens 225 and the laser 330 is maintained on resonance with the cavity 200 at all times using a Pound-Drever-Hall locking scheme.

To detect the concentration of the first species of interest, a first filter 332 is positioned between the first reflector 310 and the first Raman emission signal detector 340, wherein the first filter 332 has a high reflectance at the wavelength of the Raman emission of the first species of interest and a high transmittance at the Raman emission wavelength of the second species of interest.

To detect the concentration of the second species of interest, a second filter 325 is positioned between the first reflector 310 and the second Raman emission signal detector 335, wherein the second filter 325 has a high reflectance at the wavelength of the Raman emission of the second species of interest and a high transmittance for all other wavelengths.

The output from the first Raman emission signal detector 340 and from the second Raman emission detector 335 may be further processed to provide an output signal 370 from the dual-gas sensor.

In operation, the dual-gas sensor detects the concentration of a first species of interest and a second species of interest within a sample using Raman emission by introducing a sample into a microcavity, wherein the microcavity is formed by a first reflector that exhibits a high reflectivity near the Raman shifted emission for the first species of interest and a moderate reflectivity near the Raman shifted emission for the second species of interest and a second reflector that exhibits a high reflectivity near the Raman shifted emission for the first species of interest and a moderate reflectivity near the Raman shifted emission for the second species of interest. The second reflector is positioned at a proximate end of an optical fiber and aligned substantially parallel to the first reflector and the second reflector is separated from the first reflector by a distance to form a microcavity having a microcavity length equal to the distance between the first reflector and the second reflector, wherein the microcavity length is dependent upon the Raman transition of the first species of interest to be detected. An excitation laser beam is introduced into the microcavity to establish a double resonance condition within the microcavity, wherein an excitation wavelength of the excitation laser beam is dependent upon the microcavity length between the first reflector and the second reflector. A first Raman emission signal coupled out of the first reflector is detected to determine the concentration of the first species of interest within the sample and a second Raman emission signal coupled out of the first reflector is detected to determine the concentration of the second species of interest within the sample.

In an exemplary embodiment, the air sample to be measured is delivered directly to the hermetically sealed microcavity 200. Although applicable to a wide variety of gases, this exemplary embodiment illustrates the working principle of the dual-gas sensor for the specific case of $CO_2$ as the minority gas and $N_2$ as the majority gas. Assume that a single frequency laser 330 with $\lambda_L$=515 nm is available, which is continuously frequency tunable via an electrical input as previously described.

In the exemplary embodiment, the reflectors 305 and 310 are dielectrically coated in such a manner that the reflectivity is high (>99.99%) near both the laser frequency $\lambda_L$=515 nm and the Raman shifted emission for $CO_2$ ($\lambda_R$=555 nm) and moderate (~50%) for the Raman shifted emission from $N_2$ ($\lambda_R$=585 nm). In one embodiment, commercial multilayer dielectric coating processes commonly known in the art can be used to dielectrically coat the reflectors 305 and 310 to exhibit the desired reflectivity. Arranged in reflection from the cavity are filters 332 and 325 that select the Raman emission from each species. Single photon detectors 340 and 335 are then used to record the Raman emission signals from each of the filters to measure the concentration of both the first species of interest and the second species of interest.

It can be shown that the ratio of the Raman scattered signals from $CO_2$ and $N_2$ is particularly robust to fluctuations in laser intensity and/or wavelength, thus ensuring precise determination of the relative density of $CO_2$ and $N_2$ in the air sample.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A Raman sensor for detecting the concentration of a first species of interest and a second species of interest in a sample, the sensor comprising:
   a first reflector that exhibits a high reflectivity near the Raman shifted emission for the first species of interest and a moderate reflectivity near the Raman shifted emission for the second species of interest;
   a second reflector that exhibits a high reflectivity near the Raman shifted emission for the first species of interest and a moderate reflectivity near the Raman shifted emission for the second species of interest, positioned at a proximate end of an optical fiber and aligned substantially parallel to the first reflector, the second reflector separated from the first reflector by a distance to form a microcavity having a microcavity length equal to the distance between the first reflector and the second reflector, wherein the microcavity length is dependent upon the Raman transition of the first species of interest to be detected;
   an excitation laser positioned to emit at an excitation wavelength incident upon the first reflector and the second reflector, wherein the wavelength of the excitation laser is dependent upon the microcavity length between the first reflector and the second reflector;
   a first Raman emission signal detector positioned to receive the Raman emission coupled out of the first reflector and to detect the concentration of the first species of interest within a sample positioned between the first reflector and the second reflector; and
   a second Raman emission signal detector positioned to receive the Raman emission coupled out of the first reflector and to detect the concentration of the second species of interest within a sample positioned between the first reflector and the second reflector.

2. The sensor of claim 1, wherein the microcavity is a Fabry-Perot microcavity.

3. The sensor of claim 1, wherein optical fiber is an adjustable optical fiber, wherein the adjustable optical fiber is translatable in a direction parallel to the fiber optic axis of the optical fiber.

4. The sensor of claim 1, wherein the first reflector is fabricated on a substantially planar substrate.

5. The sensor of claim 1, wherein the second reflector conforms to a spherically shaped depression formed within a polished end of the optical fiber.

6. The sensor of claim 1, wherein the first reflector is substantially curved.

7. The sensor of claim 1, wherein the second reflector is substantially curved.

8. The sensor of claim 1, further comprising a piezoelectric transducer coupled to the second reflector, the piezoelectric transducer to adjust the length of the microcavity by translating the optical fiber in the direction parallel to the fiber's optic axis.

9. The sensor of claim 8, further comprising:
   an excitation light detector positioned at a distance from the distal end of the optical fiber,
   a feedback module coupled to the excitation light detector and to the piezoelectric transducer, the excitation light detector to receive emissions from the distal end of the optical fiber and to adjust the length of the microcavity through the feedback module.

10. The sensor of claim 1, further comprising a first filter positioned between the first reflector and the first Raman emission signal detector, the first filter having high reflectance at the wavelength of the Raman emission of the first species of interest and a high transmittance at the Raman emission wavelength of the second species of interest.

11. The sensor of claim 1, further comprising a second filter positioned between the first reflector and the second Raman emission signal detector, the second filter having high reflectance at the wavelength of the Raman emission of the second species of interest and a high transmittance at all other wavelengths.

12. The sensor of claim 1, further comprising a lens positioned between the first reflector and the excitation laser, the lens to mode match the laser beam from the excitation laser into the microcavity.

13. The sensor of claim 1, wherein the sample is selected from the group consisting of a gas and a liquid.

14. The sensor of claim 1, wherein the first Raman emission signal detector is a single photon counter.

15. The sensor of claim 1, wherein the second Raman emission signal detector is a single photon counter.

16. A Raman sensor for detecting the concentration of a first species of interest and a second species of interest in a sample, the sensor comprising:
   a first reflector that exhibits a high reflectivity near the Raman shifted emission for the first species of interest and a moderate reflectivity near the Raman shifted emission for the second species of interest;
   a second reflector that exhibits a high reflectivity near the Raman shifted emission for the first species of interest and a moderate reflectivity near the Raman shifted emission for the second species of interest, positioned at a proximate end of an optical fiber and aligned substantially parallel to the first reflector, the second reflector separated from the first reflector by a distance to form a microcavity having a microcavity length equal to the distance between the first reflector and the second reflector, wherein the microcavity length is dependent upon the Raman transition of the first species of interest to be detected;
   an excitation laser positioned to emit at an excitation wavelength incident upon the first reflector and the second reflector, wherein the wavelength of the excitation laser is dependent upon the microcavity length between the first reflector and the second reflector;
   a piezoelectric transducer coupled to the first reflector and to the second reflector, the piezoelectric transducer to adjust the length of the microcavity by translating the optical fiber in the direction parallel to the fiber's optic axis:
   an excitation light detector positioned at a distance from the distal end of the optical fiber;
   a feedback module coupled to the excitation light detector and to the piezoelectric transducer, the excitation light detector to receive emissions from the distal end of the optical fiber and to adjust the length of the microcavity through the feedback module;
   a first Raman emission signal detector positioned to receive the Raman emission coupled out of the first reflector and to detect the concentration of the first species of interest within a sample positioned between the first reflector and the second reflector;
   a first filter positioned between the first reflector and the first Raman emission signal detector, the first filter having high reflectance at the wavelength of the Raman emission of the first species of interest and a high transmittance at the Raman emission wavelength of the second species of interest;
   a second Raman emission signal detector positioned to receive the Raman emission coupled out of the first reflector and to detect the concentration of the second species of interest within a sample positioned between the first reflector and the second reflector; and a second filter positioned between the first reflector and the second Raman emission signal detector, the second filter having high reflectance at the wavelength of the Raman emission of the second species of interest and a high transmittance at all other wavelengths.

17. A method for detecting the concentration of a first species of interest and a second species of interest within a sample using Raman emission, the method comprising:

introducing a sample into a microcavity, the microcavity formed by a first reflector that exhibits a high reflectivity near the Raman shifted emission wavelength for the first species of interest and a moderate reflectivity near the Raman shifted emission wavelength for the second species of interest and a second reflector that exhibits a high reflectivity near the Raman shifted emission wavelength for the first species of interest and a moderate reflectivity near the Raman shifted emission wavelength for the second species of interest, positioned at a proximate end of an optical fiber and aligned substantially parallel to the first reflector, the second reflector separated from the first reflector by a distance to form a microcavity having a microcavity length equal to the distance between the first reflector and the second reflector, wherein the microcavity length is dependent upon the Raman transition of the first species of interest to be detected;

introducing an excitation laser beam into the microcavity to establish a double resonance condition within the microcavity, wherein an excitation wavelength of the excitation laser beam is dependent upon the microcavity length between the first reflector and the second reflector; and detecting a first Raman emission signal coupled out of the first reflector to determine the concentration of the first species of interest within the sample; and detecting a second Raman emission signal coupled out of the first reflector to determine the concentration of the second species of interest within the sample.

18. The method of claim 17, further comprising adjusting the microcavity length to establish a double resonance in the microcavity for the excitation laser as well as the Raman transition in the first species of interest.

19. The method of claim 17, wherein detecting a first Raman emission signal coupled out of the first reflector to determine the concentration of the first species of interest within the sample further comprising filtering the Raman emission signal to reflect substantially at the Raman emission wavelength of the first species of interest.

20. The method of claim 17, wherein detecting a second Raman emission signal coupled out of the first reflector to determine the concentration of the second species of interest within the sample further comprising filtering the Raman emission signal to reflect substantially at the Raman emission wavelength of the second species of interest.

* * * * *